(12) United States Patent
Sciarra

(10) Patent No.: US 7,740,588 B1
(45) Date of Patent: Jun. 22, 2010

(54) WIRELESS RESPIRATORY AND HEART RATE MONITORING SYSTEM

(76) Inventor: Michael Sciarra, 480 Joan Dr., Fairfield, CT (US) 06824

( * ) Notice: Subject to any disclaimer, the term of this patent is extended or adjusted under 35 U.S.C. 154(b) by 897 days.

(21) Appl. No.: 11/165,980

(22) Filed: Jun. 24, 2005

(51) Int. Cl.
A61B 5/02 (2006.01)
A61B 5/08 (2006.01)

(52) U.S. Cl. .................. 600/484; 600/483; 600/534; 600/535

(58) Field of Classification Search .................. 600/485, 600/500–503, 300, 322–324, 339, 342, 484, 600/534–536
See application file for complete search history.

(56) References Cited

U.S. PATENT DOCUMENTS

| 4,223,680 A | 9/1980 | Jobsis |
| 4,494,553 A | 1/1985 | Sciarra et al. |
| 4,539,440 A | 9/1985 | Sciarra |
| 4,551,149 A | 11/1985 | Sciarra |
| 4,860,766 A | 8/1989 | Sackner |
| 5,131,399 A | 7/1992 | Sciarra |
| 5,217,013 A | 6/1993 | Lewis et al. |
| 5,303,711 A | 4/1994 | Sciarra |
| 5,584,296 A | 12/1996 | Cui et al. |
| 5,673,692 A | 10/1997 | Schulze et al. |
| 5,902,235 A | 5/1999 | Lewis et al. |
| 5,919,141 A | 7/1999 | Money et al. |
| 5,954,053 A | 9/1999 | Chance et al. |
| 5,964,711 A * | 10/1999 | Voss et al. .................. 600/485 |
| 6,223,069 B1 | 4/2001 | Pfeiffer et al. |
| 6,360,122 B1 * | 3/2002 | Fischell et al. .............. 600/544 |
| 6,783,501 B2 | 8/2004 | Takahashi et al. |
| 7,177,686 B1 * | 2/2007 | Turcott ........................ 607/23 |
| 7,277,740 B2 * | 10/2007 | Rohleder et al. ............ 600/316 |
| 2001/0020395 A1 * | 9/2001 | Hubbard, Jr. ........... 73/862.041 |
| 2002/0032386 A1 * | 3/2002 | Sackner et al. ............. 600/536 |
| 2002/0188210 A1 * | 12/2002 | Aizawa ..................... 600/503 |
| 2003/0109791 A1 * | 6/2003 | Kondo et al. ............... 600/500 |
| 2005/0113657 A1 * | 5/2005 | Alarcon et al. ............. 600/342 |
| 2005/0215915 A1 * | 9/2005 | Noda et al. ................. 600/535 |

* cited by examiner

Primary Examiner—Charles A Marmor, II
Assistant Examiner—Christian Jang
(74) Attorney, Agent, or Firm—DeLio & Peterson, LLC; Peter W. Peterson

(57) ABSTRACT

A combined respiratory and heart rate sensor for a mammal has a flexible support with a surface adapted to be positioned over the skin of a mammal. A pair of inductive coil or capacitive plate elements, spaced apart by a foam spacer having openings therein, are attached to the support surface and are capable of independently sensing respiratory movement of the mammal in a direction perpendicular to the support surface and producing an output signal proportional thereto. The heart rate sensor includes an LED attached to the flexible support capable, and at least two light-detecting elements spaced apart from the LED, each capable of independently sensing light radiation reflected through the skin and capillaries from the light-emitting element and producing an output signal proportional thereto. A barrier layer attached to the support shield from the light-detecting elements light radiation that is not emitted from the LED.

27 Claims, 7 Drawing Sheets

WIRELESS RESPIRATORY AND HEART RATE MONITORING SYSTEM

BACKGROUND OF THE INVENTION

1. Field of the Invention

The present invention relates to a system and method for monitoring the respiratory and heart rate of infants and adults, as well as other mammals, and in particular to a monitoring system that may be applied to areas of the body previously thought to be unsuitable for such monitoring.

2. Description of Related Art

Heart rate monitors employing photo rather than electrode means to acquire heart rate offer the advantage of a noninvasive electrodeless method of monitoring subjects. While there are accepted and practiced means that employ photo sensors to measure heart rate, current sensor designs have only been usable in highly perfused areas of the body that have underlying arterial blood supplies very close to the skin surface. Heart rate monitoring sites have been restricted to appendages, for example, finger tips, wrist (ulner and radial arteries), ear lobes, toes and ankles. These locations also exhibit large motion artifacts when moving that can cause discontinuous monitoring of heart rate during the movement. Traditionally, most commercial heart rate photo sensors are connected by means of a wire from the subject's sensor to the monitor.

For monitoring respiration, prior art inductive or capacitance plethmography respiration sensors typically embody coils of wire or conductive material that wrap almost completely around the subject's thoracic area. Typically inductive sensors sense motion by stretching the coil, thereby causing the mutual inductance of the entire coil to respond to any motion or stretching of the coil. These types of sensors produce very reliable and artifact resistant respiration signal analogs when compared to the conventional trans-thoracic impedance (TIP) methods used in commercial monitors. However, such systems require calibration, are cumbersome, and are wired to the remote monitor. A single wraparound-type inductive coil or capacitive plate transducer generally cannot provide the required sensitivity due to the fact that the entire coil may move in response to artifact as well as respiratory efforts, which in some cases actually cancels or nullifies the desired respiratory movement detection.

Further, there is generally thought to be an incompatibility between locations on a subject's body for both heart and respiration sensors. The sites that provide good photo sensor heart wave signals (fingers, wrist, ear and foot locations) are believed to be incompatible with sites for acquiring respiration signals (thoracic, umbilicus areas). Therefore prior art attempts to combine these two methods of bio-signal acquisition have required separate sensors at distinctly different areas of the body to be measured.

SUMMARY OF THE INVENTION

Bearing in mind the problems and deficiencies of the prior art, it is therefore an object of the present invention to provide a unique sensor combining both respiration and heart rate monitoring functions that can be placed on areas of the body formerly deemed unsuitable for monitoring.

It is another object of this invention to enable the sensor to acquire heart rate and respiration signals without any wires to or from the subject being monitored.

It is yet another object of this invention to enable monitoring of the subject without any calibration or other adjustments by the care giver other than to place the sensor transducer on the subject.

Still other objects and advantages of the invention will in part be obvious and will in part be apparent from the specification.

The above and other objects, which will be apparent to those skilled in the art, are achieved in the present invention which is directed to a respiratory rate sensor for a mammal comprising a support having a flexible surface adapted to be positioned over the skin of a mammal, and at least two spaced apart inductive coils or capacitive plate elements attached to the flexible support surface being capable of sensing respiratory movement of the mammal in a direction perpendicular to the support surface and producing an output signal proportional thereto.

Preferably the sensor further includes a flexible spacer between the inductive coils or capacitive plate elements, the spacer including a plurality of separate, discrete openings therein to increase sensitivity of relative movement of the inductive coils or capacitive plate elements with respect to each other in the perpendicular direction near the openings.

In another aspect, the present invention is directed to a heart rate sensor for a mammal comprising a flexible support adapted to be positioned over the skin of a mammal, a light-emitting element attached to the flexible support capable of emitting light radiation through the skin and through capillaries beneath the skin, and at least two light-detecting elements attached to the flexible support and spaced apart from the light-emitting element. Each light-detecting element is capable of independently sensing light radiation reflected through the skin and capillaries from the light-emitting element and producing an output signal proportional thereto. The heart rate sensor further includes a barrier layer attached to the support to shield from the light-detecting elements light radiation that is not emitted from the light-emitting element.

Preferably, the barrier layer has a reflective surface facing the skin to reflect light radiation emitted from the light-emitting element. The sensor may further include a light guide for the light-emitting element to channel the light emitted from the light-emitting element through the skin and a light guide for each light-detecting element to channel the light reflected from beneath the skin. The light guides may include lens elements to focus the light radiation emitted to or from the skin, and reflective shields around each light guide to enhance light transmission therethrough.

The sensor may further include a barrier member between the light emitting element and each of the light-detecting elements. The barrier layer may comprise a reflector to guide light radiation from the light-emitting element to the light guide and reflectors to guide light radiation from the light guides to the light-emitting elements.

In a further aspect, the present invention is directed to a combined respiratory and heart rate sensor for a mammal comprising a flexible support having a surface adapted to be positioned over the skin of a mammal and a plurality of spaced apart inductive coil or capacitive plate elements attached to the support surface capable of independently sensing respiratory movement of the mammal in a direction perpendicular to the support surface and producing an output signal proportional thereto. The combined sensor further includes a light-emitting element attached to the flexible support capable of emitting light radiation through the skin and through capillaries beneath the skin, and at least two light-detecting elements attached to the flexible support and spaced apart from the light-emitting element. Each light-detecting element is capable of independently sensing light radiation reflected through the skin and capillaries from the light-emitting element and producing an output signal proportional thereto.

The sensor may further including a digital converter and radio frequency transmitter associated with the sensor to convert output signals from the inductive coil or capacitive plate elements and the light-detecting elements to digital packet form, and periodically transmit digital packets containing the output signals via radio frequency transmission to a receiver monitoring the respiratory and heart rate of the mammal. The sensor may also include an alarm function that provides with the digital packet an alarm signal if desired limits for the respiratory and heart rate of the mammal are exceeded, and provides the output signals from the inductive coil or capacitive plate elements and the light-detecting elements in real time via radio frequency transmission to the receiver if desired limits for the respiratory and heart rate of the mammal are exceeded.

BRIEF DESCRIPTION OF THE DRAWINGS

The features of the invention believed to be novel and the elements characteristic of the invention are set forth with particularity in the appended claims. The figures are for illustration purposes only and are not drawn to scale. The invention itself, however, both as to organization and method of operation, may best be understood by reference to the detailed description which follows taken in conjunction with the accompanying drawings in which:

DESCRIPTION OF THE PREFERRED EMBODIMENT(S)

In describing the preferred embodiment of the present invention, reference will be made herein to FIGS. 1-8 of the drawings in which like numerals refer to like features of the invention.

The present invention permits the wireless simultaneous physiological monitoring of both heart rate and respiration. This invention employs a sensor configuration that enables the monitoring of respiration with increased sensitivity and the monitoring of heart rate in areas of the body previously unsuitable for the acquisition of heart rate information. Additionally, the incorporation of the preferred heart rate sensor into an inductive plethmography respiration sensor provides for monitoring of the heart rate function at the optimum position for detecting respiration in infants, i.e., the umbilicus locations, since infants are for the most part "belly breathers".

Figure 1:
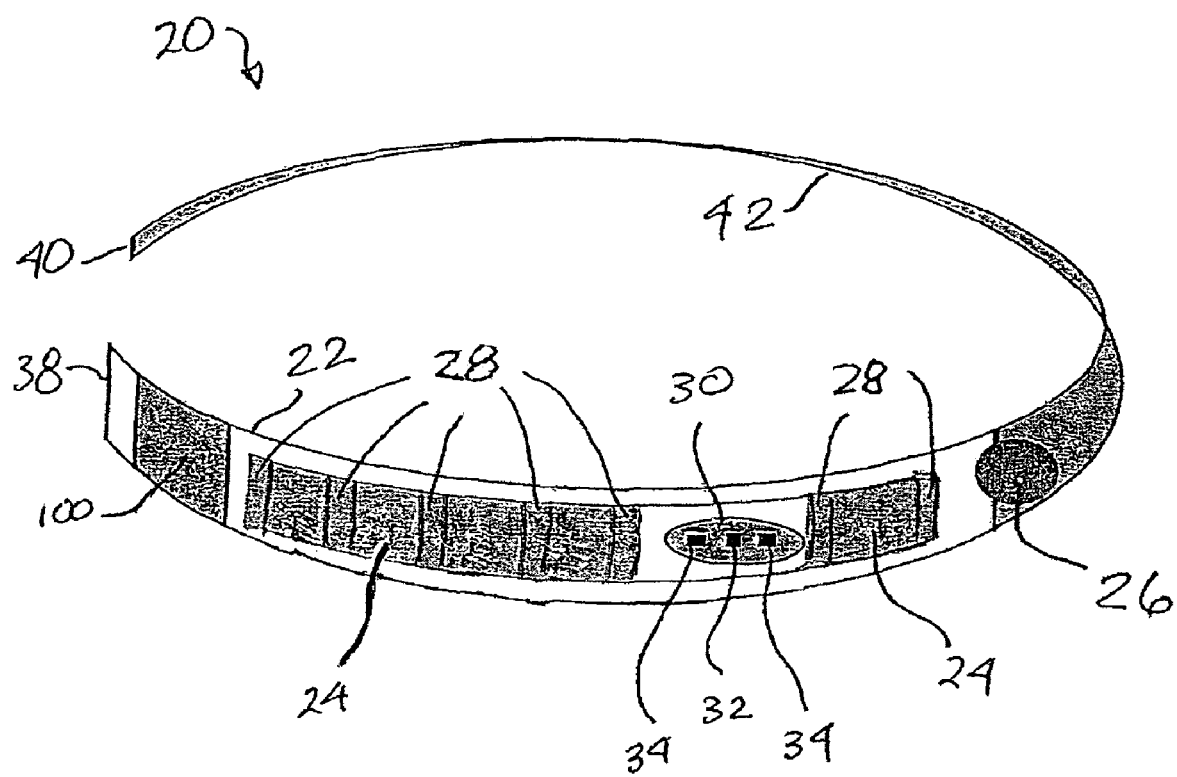
FIG. 1 is a perspective view of the preferred embodiment of the respiratory and heart monitor of the present invention.

A preferred embodiment of the respiratory and heart monitor 20 of the present invention is depicted in FIG. 1. A compliant flexible ribbon support or substrate 22 for the sensor is connected to an elastic or other band 42 that is sized to fit around the portion of the body on which monitoring is desired, for example, the abdomen. A complimentary hook-and-loop or other type fastener may be provided at band ends 38 and 40 to secure the monitor to the body. The respiratory rate sensor 24 is secured to the surface of support 22 and in one embodiment comprises two or more flat wound inductive coils positioned one above the other, optionally separated by a foam spacer. In another embodiment, the respiratory rate sensor comprises a pair of capacitive plates. The heart rate sensor 30 is likewise secured to the compliant flexible ribbon support surface and comprises a light-emitting element 32, preferably an LED, and two or more light detecting elements 34 spaced on either side of LED 32. The respiratory rate sensors 24 and heart rate sensor 30 are electrically connected by wires (not shown) to the control and processing system circuitry 100, also mounted on support 22. A battery 26 on the support powers the sensors and control circuitry. Preferably, the wiring and circuitry are printed on a compliant and flexible ribbon cable substrate to the extent possible. In use, the sensor support 22 is placed flat over and against the surface of the subject's skin.

Figure 2:
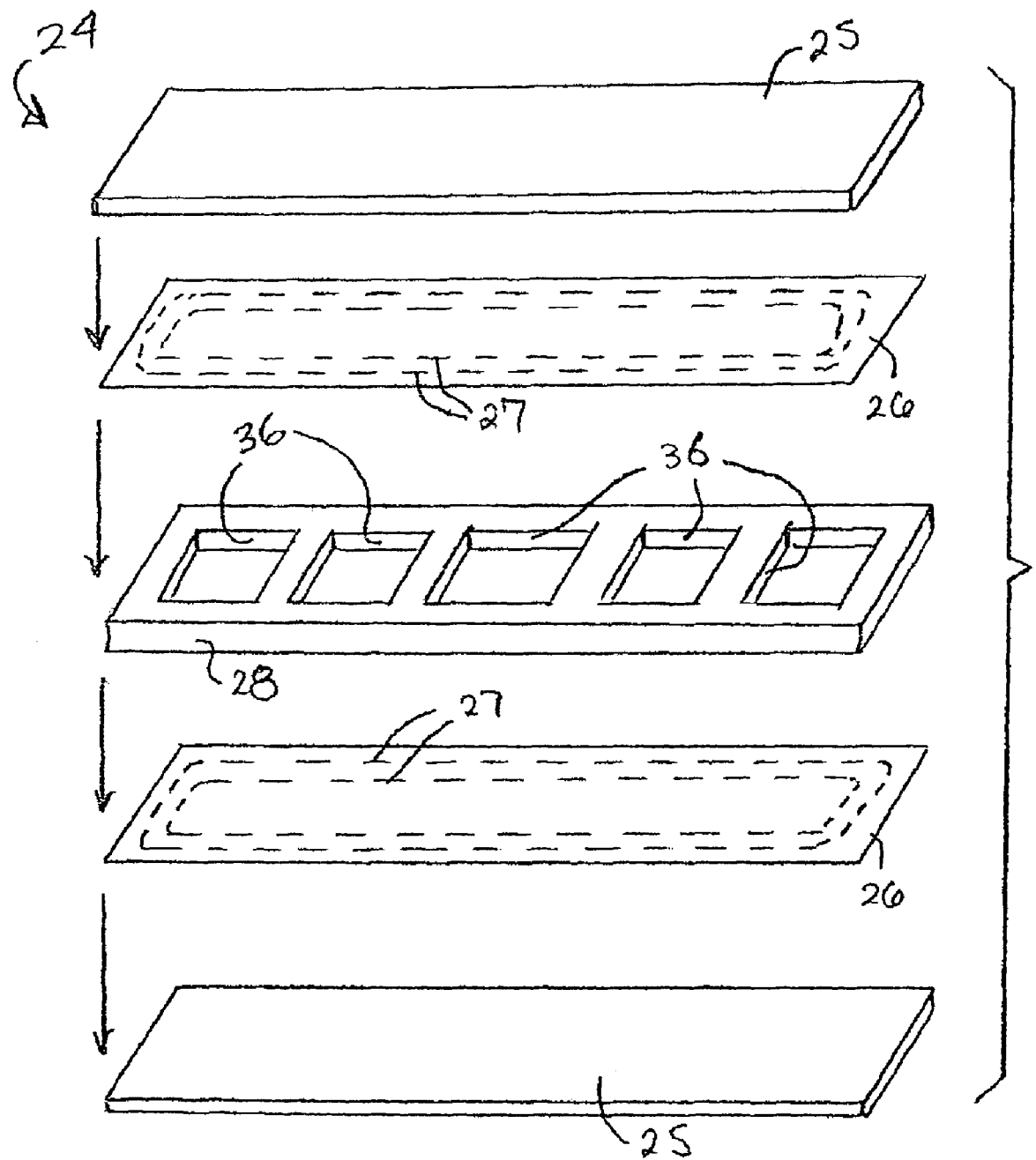
FIG. 2 is an exploded perspective view of the respiratory rate sensor used in the monitor of FIG. 1.
Figure 3:
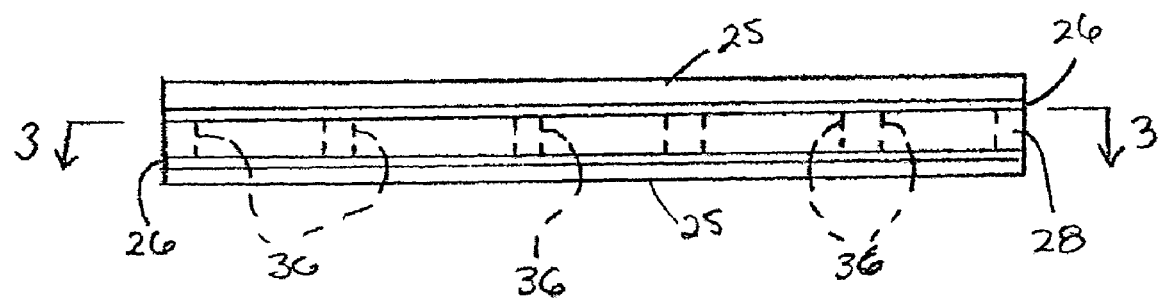
FIG. 3 is a side elevational view of the assembled respiratory rate sensor of FIG. 2.
Figure 4:
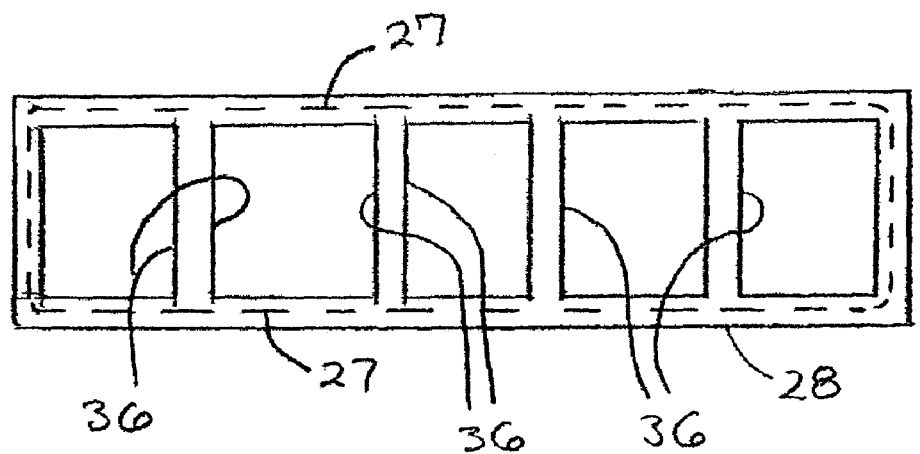
FIG. 4 is a view of the assembled respiratory sensor of FIG. 3 along lines 3-3.

As shown in more detail in FIGS. 2-4, the respiratory sensor 24 in one embodiment may include a pair of spaced apart sensor substrates 26, one over the other, and each having printed thereon an inductive coil 27. The separated coils are configured to respond to vertical or perpendicular motions to the plane of the coil and substrate, producing changes in inductance as a function of respiratory movement. Thus, instead of relying on the stretching or elongation of the coils, as in the prior art, the respiration of the wearer is sensed by compression perpendicular to the plane of the coil. A flexible spacer 28, preferably made of elastomeric material such as open cell foam having a plurality of cut-out areas—in this example rectangular 36, may be used to provide an air gap between the coils for vertical separation thereof, equal to the thickness of the flexible spacer. Other shapes and configurations for openings 36 may be employed. To provide additional protection, flexible vinyl or closed cell foam layers 25 may be provided over and under the sensor substrates.

The function of the separate, discrete openings is to permit additional deformation of the flexible material surrounding the openings in the directions in the plane of the spacer upon application of respiratory movement in the direction perpendicular to the plane of the spacer. Thus, as the flexible material is compressed, it may be deformed into the volume of the opening region, thereby modifying the load/deflection relationship to permit additional relative movement of the spaced coils toward and away from each other to create the signal and provide additional sensitivity to the respiratory sensor in that region. Alternatively, sensor substrates 26 comprise individual capacitive plates that move toward and away from each other during respiratory movement, creating a signal. In both embodiments, the vertically spaced inductive coils or capacitive plates preferably have the separate areas of additional sensitivity so that each area at the openings responds individually to perpendicular force. This provides higher sensitivity to respiratory movements. The spacer can be ribbed or otherwise cut out appropriately to provide a unique mechanical means to isolate a single inductive or capacitive sensor array into multiple isolated sensing areas.

Figure 5:
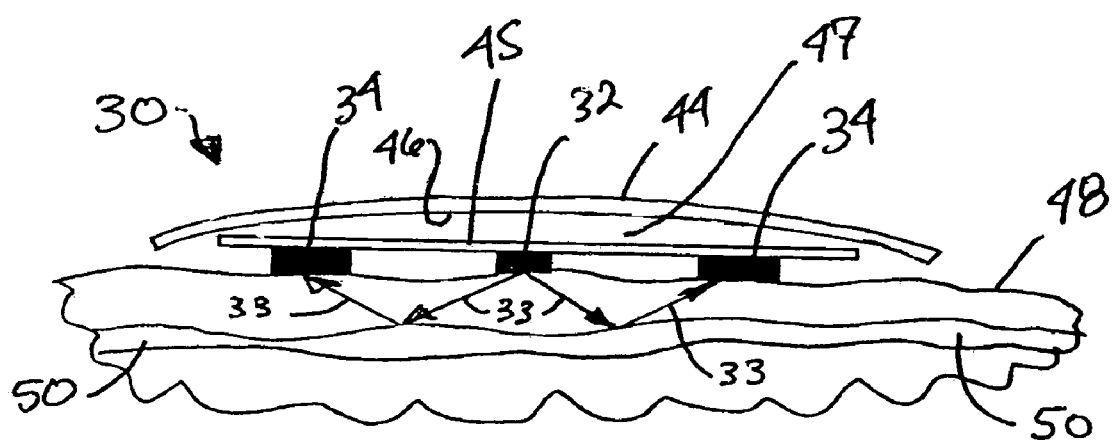
FIG. 5 is a side elevational view of one embodiment of the LED heart rate sensor used in the monitor of FIG. 1.
Figure 6:
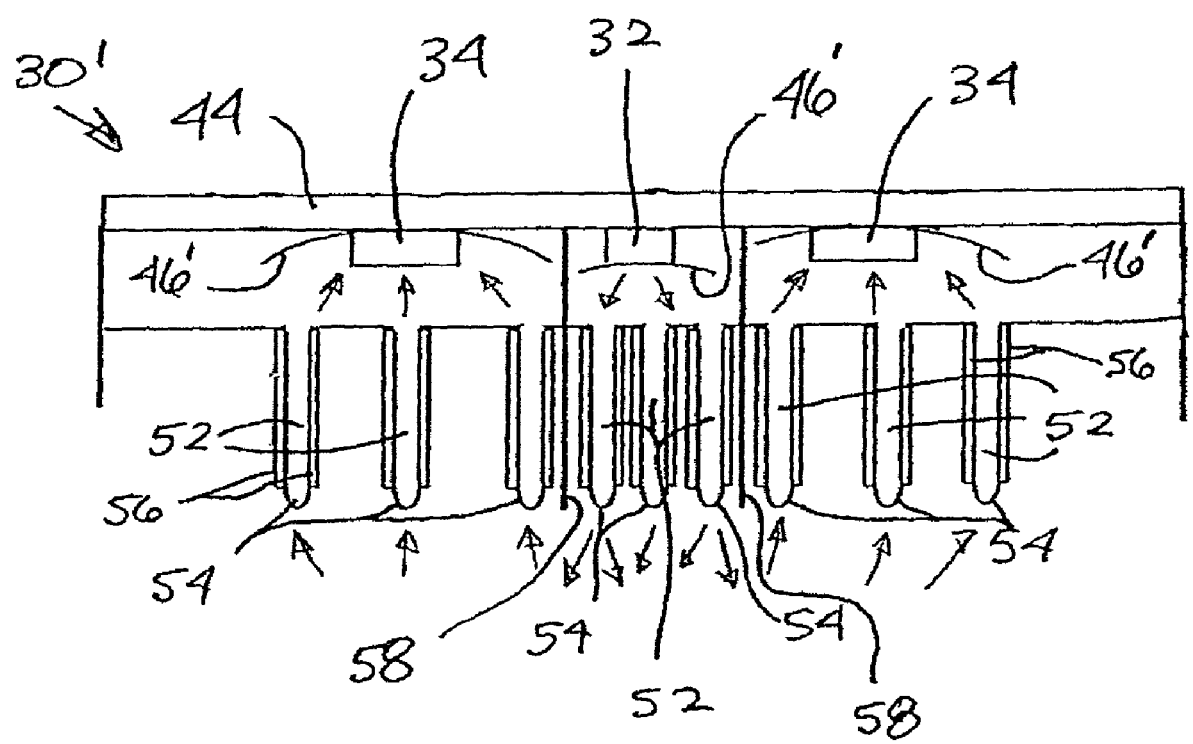
FIG. 6 is a side elevational view of another embodiment of the LED heart rate sensor that may be used in the monitor of FIG. 1.

The preferred photo plethmography sensors for measuring heart rate are shown in FIGS. 5 and 6. As used herein, the term heart rate is synonymous with pulse rate. In FIG. 5, heart rate sensor 30 includes a compliant flexible ribbon substrate 45 on which is mounted a light emitting sensor 32 comprising a high output infrared surface mount LED of sufficient power to illuminate the subject's skin to a depth of approximately 0.5 in. (12 mm). The preferred wavelength of emitted light is approximately 950 nm, in the infrared range. Spaced apart on either side of LED 32 are two or more surface mount high sensitivity PIN diode light-detecting elements, e.g., photo detectors 34, to measure the intensity of reflected infrared light that reemerges a distance away from the emitter LED 32. Such PIN diodes are able to provide quick sampling frequency, since they have little junction capacitance. Preferably, the photo detectors are at a distance less than about 0.25 in. (6 mm), more preferably about 0.187 in. (4.75 mm), from the light-emitting element. Positioning of the photo diodes greater than 6 mm apart is generally not desirable since artifacts from reparatory excursions may appear along with the desired pulse signals. This is particularly a problem in neonates wherein respiratory rate waveforms approach the frequency spectrum of the desired pulse rate waveform. It is important to the function of the heart rate sensor to exclude as much as possible any contribution to the pulse sensor output due to respiratory motion. Photo detector spacing is important to minimize this effect. In addition, by having the entire heart rate sensor on a flexible substrate, the contribution to respiratory artifact is further minimized as the emitter and photo sensors move with the abdomen in unison.

As shown in FIG. 5, the light-emitting and light-detecting elements are positioned over the skin 48 of the subject, and the infrared light rays 33 are emitted and reflected from a capillary bed 50 beneath the skin with an intensity variation proportional to the pulse or heart rate of the subject. This returned signal, when properly signal conditioned and amplified, serves to trigger a comparator that represents the heartbeat. It has been discovered that the reflected signal detected at least two different locations away from the LED emitter contains heart rate information in the pulse pressure wave that is a consequence of the Venus return and capillary bed underlying most areas of the body. Thus, this invention does not need to be placed on an arterial bed or appendage that has arterial vascularization to measure heart rate.

Preferably, the heart rate sensor incorporates an infrared barrier 44. Open cell foam 47 may fill the space between barrier 44 and sensor substrate 45. The preferred embodiment is a gold foil that is incorporated on top of the sensor, i.e., the side away from the skin, to isolate the sensing area from stray infrared radiation. This foil has a reflective surface that helps the overall sensitivity of the sensor by reflecting not only the undesired external infrared radiation, but also has a lower reflective surface 46 that traps the desired return infrared signal from beneath the skin over a larger area than would be possible based on the size of the return light-detecting elements alone.

For applications in which hair or other obstructions cover the skin of the subject, such as with a dog or other animal, another embodiment as shown in FIG. 6 may be employed, without hair removal of the animal in the desired monitoring site. In this embodiment, the reflecting surface of barrier 44 is comprised of conical reflectors 46' located at the light-emitting element 32 and light-detecting elements 34, to transmit and receive infrared light. Light guides 52 beneath the light-emitting and light-detecting elements channel the light onto and from desired areas of the skin, through any hair or similar obstruction. The guides preferably have shaped tips 54 at their lower ends which act as lenses to project and capture light between hair follicles. This enables the light to reach the skin without crushing the hair which otherwise would block light transmission, and signals may thus be acquired without hair removal. An infrared gold shield 56 may be applied to the surface of each light guide to prevent interfering interaction of the light inside and outside of the guide as well as providing isolation between each guide to enhance light transmission therethrough. Additionally, a gold coated emitter blocking barrier 58 between the light emitting element and each of the light-detecting elements shields the emitter section from the receptor sections of the heart rate sensor. Although gold film is described in this embodiment, other infrared blocking films could also be utilized to perform this function.

Figure 7:
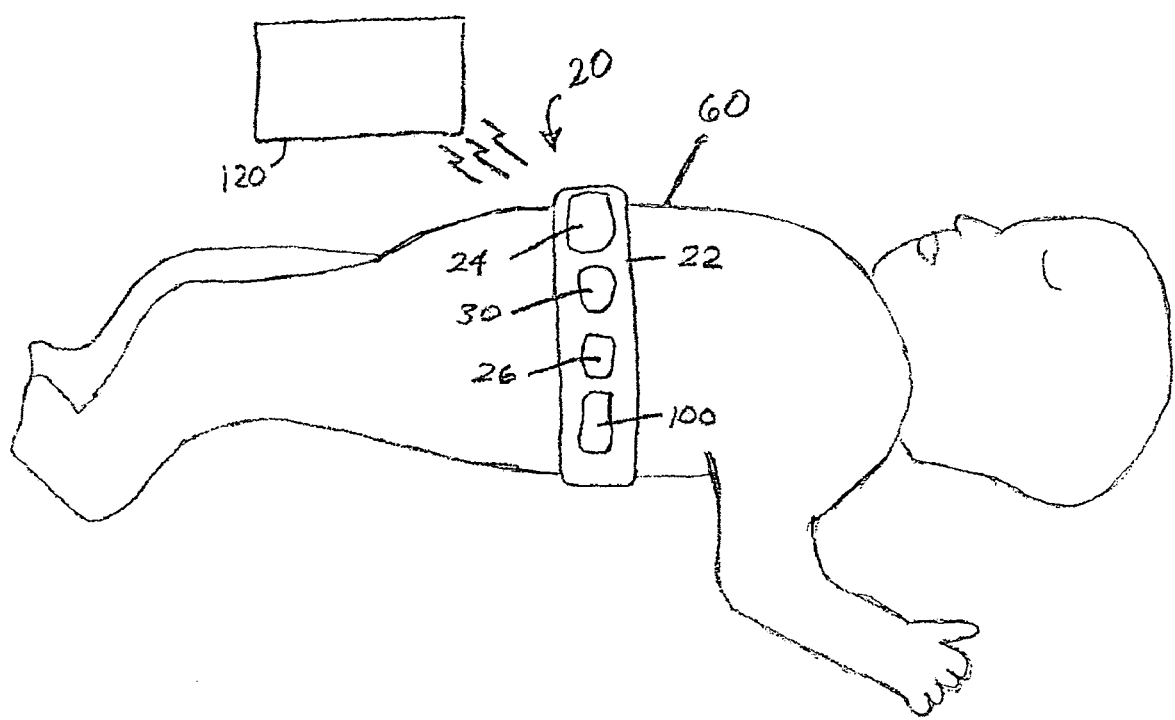
FIG. 7 is a perspective view of the respiratory and heart monitor of FIG. 1 worn by an infant.

FIG. 7 depicts the preferred combined respiratory and heart monitor 20 of the present invention as worn by a neonatal infant about its abdomen 60. The monitor 20 may be placed at any desired part of the body that receives sufficient respiratory movement, and enables heart rate to be monitored at the same time. After processing by control system circuitry 100, the signals indicating the respiratory and heart rates are sent wirelessly to a patient display monitor 120 for observation.

Figure 8:
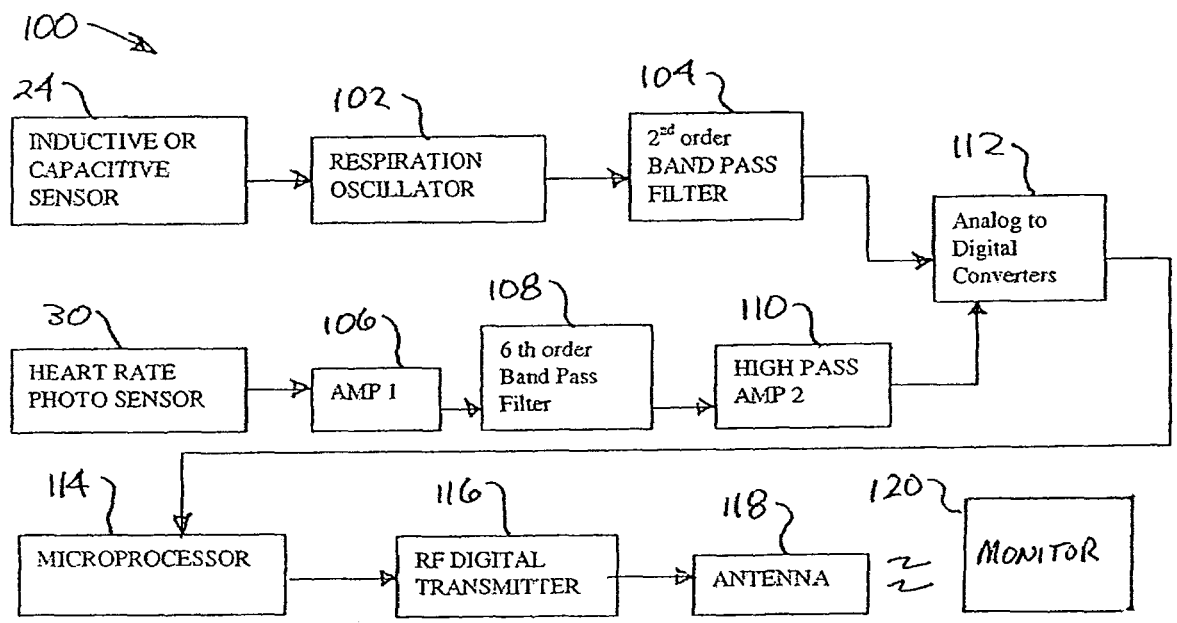
FIG. 8 is a schematic of the respiratory and heart monitor system and method used in the monitor of FIG. 1.

The method of operation of the preferred monitor control system circuitry 100 is described in FIG. 8. The inductive or capacitive respiratory sensor 24 produces a change in the nominal oscillator frequency of a respiration oscillator 102. The spacer effectively mechanically isolates discrete areas of the inductive coils at the areas of the spacer openings and, in so doing, provides multiple sensing areas within a single transducing sensor. Further, the respiratory sensor spacer by design unloads the compression force that would otherwise be required to compress the sensor in response to a respiratory movement. This makes the respiratory sensor more sensitive to the desired perpendicular motion and compression of the sensor due to respiratory movement than would be possible with a single continuous elastic spacer. The inclusion of cut-out areas within the spacer provides this mechanical amplification function.

Changes in inductance or capacitance of respiratory sensor 24 modify the frequency of the oscillator in a manner directly proportional to the compression or decompression of the sensor in response to chest or abdomen motion. A second order band pass post filter 104 cleans up any residual jitter or artifact remaining on the oscillator blocks output. The post filter 104 output is then presented to an analog to digital converter 112 where it is digitized and presented to a microprocessor 114 input for further processing.

A software routine run by the microprocessor takes this digitized representation of the oscillator frequency and performs a digital phase lock loop function. This software then extracts the voltage controlled oscillator (VCO) component, which is the demodulated voltage representing change in the frequency of oscillator 102. This is a DC voltage that reflects only changes in the oscillator as a function of respiratory motion. The software then compares this voltage to a reference voltage set internally by the software, thereby effectively performing a comparator function. This digital comparator output represents each individual breath. The comparator output is then analyzed and a computed rate per minute is saved for incorporation into a data transmission. When not in an alarm condition (described further below), updates occur periodically, e.g., every five seconds. Additionally a first in, first out (FIFO) minute rotating buffer records the previous time span, e.g., three minutes, continually during monitoring until an alarm condition is detected.

Simultaneously with the operation of the respiratory sensor, the heart rate infrared LED emitter is pulsed at a fixed frequency and duty cycle so as to save power, as compared to a continuously powered LED. The photo heart rate sensor 30 output is fed to a first amplifier 106 to boost the signal in preparation for a sixth order band pass filtering 108. Band pass filter 108 limits the frequencies that are undesired for the intended application by attenuating both low and high frequencies so as to pass only a relatively small bandwidth of 4-10 Hz to detect if the pulse pressure signal is present. The band pass is designed to be centered about the maximum spectral energy produced within the pulse pressure waveform detected by the sensors and representing the desired heart waveform, which may be determined without undue experimentation. After band passing, further amplification occurs in a second amplifier 110, which preferably also includes a high-speed integrator and amp to provide additional high pass isolation and gain. Further signal processing removes any residual artifacts from stray light and motion interference by sampling the photo sensor during the time the photo emitter is off. The A/D samples are taken before the emitter is turned on, and immediately after the emitter is turned off. This data is subtracted from the data provided while the emitter is switched on resulting in only the data contributed by the actual pulse waveform. At this point, the heart rate signal is processed by A/D converter 112 and microprocessor 114 essentially the same manner as for the respiration waveform described previously. The method of the present invention for processing respiratory and heart rate signals may be implemented by a computer program or software incorporating the process steps and instructions described above in otherwise conventional program code and stored on an otherwise conventional program storage device accessible by microprocessor 114.

After signal processing by the microprocessor, the software assembles the respiratory and heart rate data into a discrete digital data packet form for transmission, preferably wireless transmission by a radio frequency transmitter 116 through antenna 118, both also incorporated into support 22. The packet size depends on the amount of data to be transmitted. In one embodiment, a 32 bit data packet may be transmitted every five seconds during nominal, no-alarm operation. The packet may contain the encoded heart rate, respiration rate, starting header, battery status, patient ID and error correction bits. The data packets are fed to the modulation inputs of transmitter 116 for wireless transmission to the receiving display monitor 120. The transmitter can be either AM, FM or spread spectrum, and operate within allowed FCC frequencies. Display monitor 120 receives and decodes the digital transmissions from transmitter 116 and displays respiratory and heart rate along with alarms and user limit settings in accordance with standard medical monitoring practices.

Preferably, the software run in microprocessor 114 incorporates an alarm routine. This is accomplished by setting bounds or limits about the acceptable breathing or heart rate rates allowed for the subject. If the output of the comparator is higher or lower than the boundary limits, the system may place an alarm bit into the data stream to be transmitted to the display monitor 120 to alert it to an alarm condition, and set the transmitter 116 into continuous mode. During an alarm condition the data packet is configured to carry the additional real time waveform data from both heart and respiratory waveforms, and real time transmission of data occurs. Thus, in the case of respiration monitoring, the serial data stream representing the demodulated DC respiratory waveform from the VCO is transmitted continually. In case of heart rate monitoring, a serial data stream representing the heart rate is transmitted continually. This affords the clinician viewing the monitor access to the actual respiratory and heart rate waveforms in real time during the event.

Additionally, microprocessor 114 may access a program storage device on substrate 22, for example, a semiconductor chip, a read-only memory, or magnetic media such as a computer hard drive, that continuously records respiratory and heart rate data for a predetermined time period. Subsequent to the alarm event, the clinician can depress a membrane switch on the transducer that will transmit the respiratory or heart rate waveform data for a desired time period prior to the event, for example, three minutes, thus allowing the clinician to view recorded data leading to the alarm condition.

Monitor 20 may have a separate control and processing circuitry section 100 and battery supply 26. In another embodiment, monitor 20 may have a combined detachable module comprising all the control and processing circuitry and battery power supply. The advantage of the separate module is that the respiratory and heart rate sensors could be made disposable, while the control and processing circuitry and battery sections would be reusable.

The respiratory and heart monitor of the present invention may be used to measure heart rate and respiration of humans, such as infants or adults, as well as other mammals such as dogs or other animals.

The multiple sensing areas provided by the vertical force-sensing inductive coil or capacitive sensors of the present invention overcome the problem of signal cancellation by wraparound-type respiratory sensors. Moreover, the improved heart rate sensors enable monitoring of heart rate at the same locations on a subject's body thought to be suitable only for respiration monitoring. Clinical evaluations of the present invention have shown that the system and method performs with better artifact rejection; less set up time, and is less invasive than other methods currently used in the monitoring or respiration and heart rate.

While the present invention has been particularly described, in conjunction with a specific preferred embodiment, it is evident that many alternatives, modifications and variations will be apparent to those skilled in the art in light of the foregoing description. It is therefore contemplated that the appended claims will embrace any such alternatives, modifications and variations as falling within the true scope and spirit of the present invention.

Thus, having described the invention, what is claimed is:

1. A respiratory and heart rate sensor for a mammal comprising:
    a flexible support having a surface adapted to be positioned over the skin of a mammal;
    a pair of inductive coil or capacitive plate elements attached to the support surface, each inductive coil or capacitive plate element being spaced apart from a next inductive coil or capacitive plate element, the inductive coil or capacitive plate elements being capable of sensing respiratory movement of the mammal in a direction perpendicular to the support surface by relative movement toward and away from each other in the perpendicular direction, without stretching or elongation, and producing an output signal proportional thereto;
    a light-emitting element attached to the flexible support capable of emitting light radiation through the skin and through capillaries beneath the skin; and
    at least two light-detecting elements attached to the flexible support and spaced apart from the light-emitting element, each light-detecting element capable of independently sensing light radiation reflected through the skin and capillaries from the light-emitting element and producing an output signal proportional thereto.

2. The sensor of claim 1 further including a digital converter and radio frequency transmitter associated with the sensor to convert output signals from the inductive coil or capacitive plate elements and the light-detecting elements to digital packet form and periodically transmitting digital packets containing the output signals via radio frequency transmission to a receiver monitoring the respiratory and heart rate of the mammal.

3. The sensor of claim 2 wherein the sensor includes an alarm function that provides with the digital packet an alarm signal if desired limits for the respiratory and heart rate of the mammal are exceeded, and provides the output signals from the inductive coil or capacitive plate elements and the light-detecting elements in real time via radio frequency transmission to the receiver if desired limits for the respiratory and heart rate of the mammal are exceeded.

4. The sensor of claim 1 further including a flexible spacer between each of the inductive coil or capacitive plate elements, the spacer including a plurality of separate, discrete openings therein for relative movement of the inductive coil or capacitive plate elements with respect to each other in the perpendicular direction near the openings.

5. A method of monitoring respiratory and heart rates of a mammal comprising:
  applying over the skin of a mammal a flexible support including: i) a pair of inductive coil or capacitive plate elements attached to a surface thereof, each inductive coil or capacitive plate element being spaced apart from a next inductive coil or capacitive plate element, the inductive coil or capacitive plate elements being capable of sensing respiratory movement of the mammal in a direction perpendicular to the sensor surface by relative movement toward and away from each other in the perpendicular direction, without stretching or elongation, and producing an output signal proportional thereto, ii) a light-emitting element capable of emitting light radiation through the skin and through capillaries beneath the skin, and iii) at least two light-detecting elements spaced apart from the light-emitting element, each light-detecting element capable of independently sensing light radiation reflected through the skin and capillaries from the light-emitting element and producing an output signal proportional thereto;
  measuring output signals from the inductive coil or capacitive plate elements to determine the respiratory rate of the mammal; and
  measuring output signals from the light-detecting elements to determine the heart rate of the mammal.

6. The method of claim 5 wherein the light emitting and light-detecting elements are not placed over an artery beneath the skin of the mammal.

7. The method of claim 5 wherein a reference oscillator frequency is determined by the inductive or capacitive changes caused by respiratory movement, and wherein the output signals from the inductive coil or capacitive plate elements are used to change the frequency of the oscillating signal to determine the respiratory rate of the mammal.

8. The method of claim 5 wherein the output signal from the light-detecting elements is modified to attenuate high and low frequencies thereof, and wherein the remaining output signal is amplified to determine the heart rate of the mammal.

9. The method of claim 5 further including recording a first in, first out rotating buffer a previous time span of respiratory and heart rate data and setting an alarm to be triggered corresponding to desired limits for the respiratory and heart rate of the mammal and, if the alarm is triggered, permitting the reviewing of the previous time span of respiratory or heart rate data recorded prior to triggering of the alarm.

10. The method of claim 5 further including converting output signals from the inductive coil or capacitive plate elements and the light-detecting elements to digital packet form and periodically transmitting digital packets containing the output signals via radio frequency transmission to a receiver monitoring the respiratory and heart rate of the mammal.

11. The method of claim 5 further including a flexible spacer between each of the inductive coil or capacitive plate elements, the spacer including a plurality of separate, discrete openings therein.

12. The method of claim 10 further including providing with a digital packet an alarm signal if desired limits for the respiratory and heart rate of the mammal are exceeded.

13. The method of claim 12 further including providing the output signals from the inductive coil or capacitive plate elements and the light-detecting elements in real time via radio frequency transmission to the receiver if desired limits for the respiratory and heart rate of the mammal are exceeded.

14. A respiratory rate sensor for a mammal comprising:
  a support having a flexible surface adapted to be positioned over the skin of a mammal; and
  two inductive coils or capacitive plate elements attached to the flexible support surface, each inductive coil or capacitive plate element being separated from a next inductive coil or capacitive plate element by a distance, the inductive coil or capacitive plate elements being capable of sensing respiratory movement of the mammal in a direction perpendicular to the support surface by relative movement toward and away from each other in the perpendicular direction, without stretching or elongation, and producing an output signal proportional thereto.

15. The sensor of claim 14 wherein the elements are inductive coils and further including a flexible spacer between the inductive coils, the spacer including a plurality of separate, discrete openings therein.

16. The sensor of claim 14 wherein the elements are capacitive plate elements mounted on the support surface and further including a flexible spacer between the capacitive plates, the spacer including a plurality of separate, discrete openings therein.

17. A heart rate sensor for a mammal comprising:
  a compliant flexible ribbon support adapted to be positioned over the skin of a mammal;
  a light-emitting element attached to a first side of the compliant flexible ribbon support capable of emitting light radiation through the skin and through capillaries beneath the skin;
  at least two light-detecting elements attached to the first side of the compliant flexible ribbon support and spaced apart from the light-emitting element, each light-detecting element capable of independently sensing light radiation reflected through the skin and capillaries from the light-emitting element and producing an output signal proportional thereto; a barrier layer attached to a second side of the support; and
  the barrier layer having a reflective material attached to and extending along the barrier layer to shield from the light-detecting elements external light radiation which is not emitted from the light-emitting element.

18. The sensor of claim 17 wherein the barrier layer has a reflective surface facing the skin to reflect light radiation emitted from the light-emitting element.

19. The sensor of claim 17 further including a light guide for the light-emitting element to channel the light emitted from the light-emitting element through the skin and a separate light guide for each light-detecting element to channel the light reflected from beneath the skin.

20. The sensor of claim 19 wherein the light guides include lens elements to focus the light radiation emitted to or from the skin.

21. The sensor of claim 19 wherein the light guides include reflective shields around each light guide to enhance light transmission therethrough.

22. The sensor of claim 19 further including a barrier member between the light emitting element and each of the light-detecting elements.

23. The sensor of claim 19 wherein the barrier layer comprises a reflector to guide light radiation from the light-emitting element to the light guide and reflectors to guide light radiation from the light guides to the light-detecting elements.

24. The sensor of claim 17 wherein the light emitting element and each of the light-detecting elements are secured to a surface of the compliant flexible ribbon support.

25. A respiratory rate sensor for a mammal comprising:
 a support having a flexible surface adapted to be positioned over the skin of a mammal; and
 a pair of inductive coils or capacitive plate elements attached to the flexible support surface, the inductive coil or capacitive plate elements being separated from each other by a flexible spacer made of elastomeric material, the flexible spacer including a plurality of separate, discrete openings therein; and
 the inductive coil or capacitive plate elements sensing respiratory movement of the mammal in a direction perpendicular to the support surface by relative movement of the inductive coil or capacitive plate elements toward and away from each other in the perpendicular direction, without stretching or elongation, to produce an output signal proportional thereto.

26. The sensor of claim 25 wherein the elements are inductive coils.

27. The sensor of claim 25 wherein the elements are capacitive plate elements.

* * * * *